Dec. 21, 1954 R. S. MOORE Plant Pat. 1,335

ROSE PLANT

Filed Feb. 26, 1954

WITNESS

Addison E. Avery

INVENTOR

Ralph S. Moore

Webster & Webster

ATTYS.

United States Patent Office

Plant Pat. 1,335
Patented Dec. 21, 1954

1,335

ROSE PLANT

Ralph S. Moore, Visalia, Calif.

Application February 26, 1954, Serial No. 412,973

1 Claim. (Cl. 47—61)

This invention relates to a new and distinct variety of miniature rose plant; the variety being a seedling from Oakington Ruby (unpatented miniature) as the seed parent, and the pollen parent being unknown.

The present variety of rose plant bears flowers having a bi-color characteristic; the flowers being very double and a deep or rose pink on the upper side and a lighter or silver pink on the under side. This bi-coloring of the flowers makes them most distinctive and attractive.

Another distinctive characteristic of the present variety of rose plant is that it is completely free of thorns on all twigs and canes, and additionally the variety is seedless.

The instant variety of rose plant grows readily from cuttings, and produces a good, well branched, dwarf, bushy plant, which averages ten to twelve inches in height.

The variety has carried forward the freedom of bloom and the general plant habits of the Oakington Ruby, excepting the absence of thorns, as above; the variety growing and blooming well under glass, and being adapted for garden decoration, and as a pot plant.

The original seedling of the instant variety was originated in my nursery at Visalia, California, and subsequently was asexually reproduced—in such nursery—by cuttings; the reproductions having been found to carry forward all of the characteristics of the seedling parent.

Figure 2:
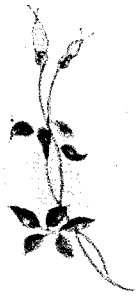
Figs. 2 and 3 are views showing buds in the preliminary stages of opening.
Figure 1:
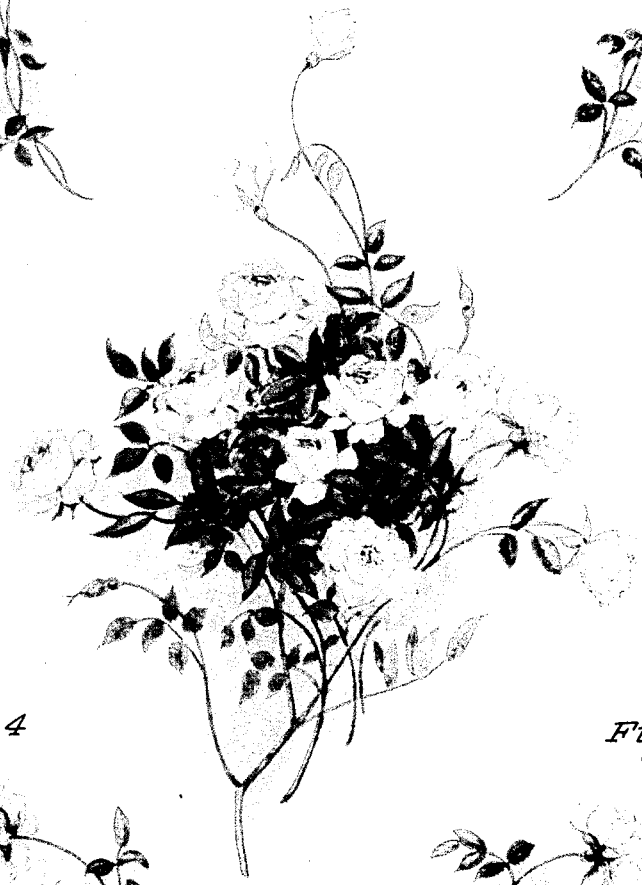
Fig. 1 is an elevation showing a number of the flowers and buds of the variety, together with leaves and stems.
Figure 3:
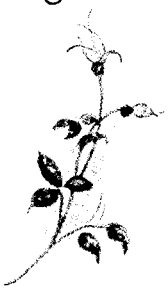
Figure 4:
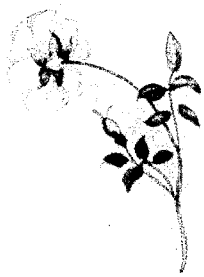
Figs. 4 and 5 are views of individual flowers showing particularly the silver pink color of the under side of the petals.
Figure 5:
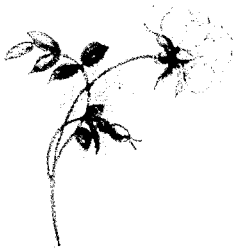

Referring now specifically to the new and distinct variety of rose plant, the following is a detailed description thereof in outline; all major color plate identifications being by Maerz and Paul Dictionary of Color:

Type: Dwarf; bush; hardy. Grows and blooms well under glass. Garden decoration. Pot plant.

Class: Miniature.

Flowers:

*Continuity.*—Continuous.

*Fragrance.*—Moderate.

Flowers borne: Usually singly, but sometimes several (2–4) to stem. Irregular cluster. Normal short stem.

Quantity of bloom: Abundant both outdoors and in greenhouse.

Bud:

*Peduncle.*—Short; medium; erect; reddish green; almost smooth; few hairs.

*Before calyx breaks.*—Size—small. Form—oval, with foliaceous appendages on the surface of the bud. Color—green; sometimes shaded reddish.

*As calyx breaks.*—Color—deep pink.

*As first petal opens.*—Size—small. Form—ovoid. Color—top side—deep or rose pink (49–K–1 to 49–L–1); under side—lighter or silver pink (49–E–2).

Opening—retarded by cold weather.

Bloom:

*Size.*—When fully opened—1″ average in diameter.

*Petalage.*—Very double, with from fifty to sixty petals arranged regularly.

*Form.*—At first full; becoming globular; becoming later loosely rolled outward.

Petals: Thin. Satiny both sides.

*Shape.*—Outside—obovate. Intermediate—obviate. Inside—lanceolate.

*Color.*—Top side—deep or rose pink (49–K–1 to 49–L–1). Under side—Lighter or silver pink (49–E–2).

After the flowers have been open several days the deep pink of the top side of the petals tends to lighten somewhat.

*Behavior.*—Old flowers generally drop off.

*Flower longevity.*—Bush in garden—three to five days. Cut roses indoors—two to three days.

Reproductive organs:

*Stamens.*—None.

*Filaments.*—None.

*Pollen.*—None.

*Pistils.*—Few.

*Styles.*—Uneven.

*Stigma.*—None or imperfect.

*Hips.*—None.

*Seeds.*—None.

PLANT

Foliage:

*Leaves.*—Compound of seven leaflets average. Small; soft; normal.

*Leaflets.*—Oval. Apex—acute. Base—round. Margin—serrate.

*Color.*—Normal.

Upper surface—green (22–L–12 shading to 22–L–8).

Under surface—lighter green (21–I–7).

*Rachis.*—Light.

Upper side—smooth, grooved.

Under side—two or three very tiny thorns.

*Stipules.*—Short. Medium width with short points turning out at an angle of about 45°.

Growth:

*Habit.*—Dwarf; bushy; much branched.

*Growth.*—Free.

*Canes.*—Light to medium.

*Main stems.* — Color — green. Thorns — none. Prickles—none. Hairs—none.

*Branches.* — Color — green. Thorns — none. Prickles—none. Hairs—none.

*New shoots.* — Color — green. Thorns — none. Prickles—none. Hairs—none.

The miniature rose plant and its flowers as herein described may vary in slight detail due to climatic and soil conditions under which the variety may be grown.

Having thus described my invention, I claim:

A new and distinct variety of miniature rose plant substantially as described and illustrated, characterized—in comparison with the seed parent Oakington Ruby—by flowers more double than those of said parent, and by bi-coloring, the petals being a deep rose on the top side and a lighter silver pink on the under side; the plant averaging ten to twelve inches in height, being much branched, thornless on all twigs and canes, and seedless.

No references cited.